(12) United States Patent
Choi et al.

(10) Patent No.: US 7,083,812 B2
(45) Date of Patent: Aug. 1, 2006

(54) CHEMICAL LIBRARY PREPARATION METHOD FROM NATURAL PRODUCT

(75) Inventors: Ho-Il Choi, Taejon (KR); Seung-Gu Chang, Taejon (KR); Sun-Young Kim, Taejon (KR); Seong-Kyu Kim, Taejon (KR); Jeong-Kyu Bang, Taejon (KR)

(73) Assignee: Peptron, Inc., Taejon (KR)

( * ) Notice: Subject to any disclaimer, the term of this patent is extended or adjusted under 35 U.S.C. 154(b) by 0 days.

(21) Appl. No.: 10/112,120

(22) Filed: Mar. 29, 2002

(65) Prior Publication Data

US 2003/0133997 A1    Jul. 17, 2003

Related U.S. Application Data

(63) Continuation of application No. PCT/KR00/01095, filed on Sep. 30, 1999.

(30) Foreign Application Priority Data

Sep. 30, 1999  (KR) .............................. 1999-42137
Sep. 29, 2000  (KR) .............................. 2000-57197

(51) Int. Cl.
*A61K 35/78* (2006.01)
*C12N 11/00* (2006.01)
*C12N 11/06* (2006.01)

(52) U.S. Cl. ...................... 424/725; 435/174; 435/181

(58) Field of Classification Search ................ 424/725; 435/174, 175, 180, 181
See application file for complete search history.

(56) References Cited

U.S. PATENT DOCUMENTS

| | | | |
|---|---|---|---|
| 3,031,380 A * | 4/1962 | Minagawa et al. ......... 435/447 |
| 3,597,220 A * | 8/1971 | Weinrich et al. ............... 426/12 |
| 3,821,084 A * | 6/1974 | Matthews .................... 435/181 |
| 3,834,990 A * | 9/1974 | Werle et al. ................. 435/197 |
| 3,995,031 A * | 11/1976 | Henkin et al. .................. 514/2 |
| 4,013,511 A * | 3/1977 | Goldstein et al. ............ 435/181 |
| 4,066,505 A * | 1/1978 | Schneider .................... 435/178 |
| 4,131,727 A * | 12/1978 | Lange et al. ................. 536/112 |
| 5,200,186 A * | 4/1993 | Gabetta et al. ............. 424/732 |
| 5,449,823 A * | 9/1995 | Lerch .......................... 562/577 |
| 5,888,966 A * | 3/1999 | Larsen et al. ................... 514/2 |
| 6,194,469 B1 * | 2/2001 | Nair et al. ..................... 514/27 |
| 6,274,358 B1 * | 8/2001 | Holtz et al. ................. 435/157 |
| 6,428,818 B1 * | 8/2002 | Morre et al. ................. 424/729 |
| 6,495,140 B1 * | 12/2002 | Collins et al. .............. 424/745 |
| 6,602,692 B1 * | 8/2003 | Glusenkamp et al. ....... 435/181 |

FOREIGN PATENT DOCUMENTS

| | | | |
|---|---|---|---|
| DE | 19653730 | * | 6/1998 |
| JP | 56158800 | * | 12/1981 |
| WO | WO/9729091 A1 | | 8/1997 |

OTHER PUBLICATIONS

Mateo et al. Enzyme and Microbial Teachnology. 2000. vol. 26, No. 7, pp. 509-515, BIOENG Abstract enclosed.*
Nielsen et al., 1996, Tetrahedron Letters,37:8349-8442.

* cited by examiner

*Primary Examiner*—Christopher R. Tate
(74) *Attorney, Agent, or Firm*—Cheryl H. Agris (57) ABSTRACT

The present invention relates to a preparation method of a general library and a focused library from crude extracts of natural products including herbal drugs, said libraries, and the method for developing new drugs such as an anticancer drug and new substances using said libraries. The method comprises step of attaching crude extract of natural products to the solid phase resin, and step of washing the compounds and reactants that are not attached.

4 Claims, 11 Drawing Sheets

Fig. 1

Merrifield resin 80℃,0℃
Ref 1,2

Wang or TentaGel S PHB
Cyclohexane/CH₂Cl₂/r.t

Hydroxymetyl resin
N-methylmorpholine
Ref 4

References

1. Kick, E.K.;Ellman,J.A.;J.Med.Chen.,1995,38,1427-1430

2. Thompson,L.A.;Ellman,J.A.,,Tetrahedron Lett.,1994,35,9333-9336

3. Hanessian,S,;Xie,F.;Tetrahedron Lett.1998,39,733-736

Fig. 2a

References

5. Dressman,B.A.;Spangle,L.A.,;Kaldor,S.W.;Tetrahedron Lett., 1996,37,937-940

6. Kaljuste,K.;Unden,A.;Tetrahedron Lett.,37,3031-3034

Fig. 2b

Glass support
split-mix library
Ref 7

MeO-PED soluble
polymer. Ref 8

References

7. Fathi, R.;Patel, R.;Cook,A.F.;Molecular Diversity 1996,2,125-134
8. Han,H.;Wolfe,M.M.; Brenner, S.;Janda,K.D.;Proc.Natl.Acad.Sci.USA,

Fig. 3

TentaGel HC(Ome)
Ref 9

Wang resin, DMF/piperidine
Ref 10

References

9. Look, G.C.; Murphy.M.M.;Campell,D.A.;Ttrahedron Leff., 1995,36,2937-2940

10. Zaragoza,F.,Tetrahedron Lett., 1995,36,8677-8678

Fig. 4

Wang resin, DMF
Ref 11

HMPB-MBHA and Wang resin
Ref 12

References

11. Perumattam,J.;Chakravarty,S.;McEnroe,G.A.;Gohring,R.R.; Mavunkel,B.;Suravajjala,S.;Smith,W.W.;Chen,B.;Molecular Diversity 1998,3,121-128

12. Floyd,C.D.;Lewis,C.N.;Patel,S.R.;Whittaker,M.;Tetrahedron Lett,1996,37

Chloromethyl Resin

Fig. 6b

Wang-Cl Resin

Fig. 6c

2-Chlorotrityl Chloride Resin

CHEMICAL LIBRARY PREPARATION METHOD FROM NATURAL PRODUCT

This application is a continuation of PCT/KR00/01095 filed Sep. 30, 1999 and also claims priority from Korean application nos. 199-42137 and 2000-57197 filed Sep. 30, 1999 and Sep. 29, 2000 respectively under 35 U.S.C. 119 (a)–(d).

TECHNICAL FIELD

The present invention relates to a chemical library preparation method, said library and the method of use thereof. More particularly, the present invention relates to a preparation method of general and focused chemical libraries using solid phase synthesis method from crude extracts of natural products including herbal drugs, and it also relates to said libraries and the method for developing new drugs, such as anticancer drugs and functional biological substances, using said libraries.

BACKGROUND OF INVENTION

Conventional libraries, such as peptide libraries which have been widely used in the field of combinatorial chemistry or new drug development, generally consists of amino acids whose chemical structures are already known. Conventional libraries have largely depended on the method of manufacturing various combinations of compounds by repeatedly combining structurally diverse compounds.

However, conventional libraries have limits in diversity since compound components constituting the library are constructed from chemical synthesis.

In addition, conventional libraries have been extensively explored by many researchers in the field of new drug development.

On the contrary, compounds in the natural products containing herbal drugs are great in numbers and frequently contain compounds, such as optical isomer, that are difficult to synthesize using current organic synthesis technology. Compounds in the natural products possess much more variety in property and chemical structure than the compounds synthesized by organic synthesis.

Therefore, considerable efforts have been devoted by many researchers to search and discover useful substances from natural products. But these researches have generally been directed to obtaining useful compounds using the general method of isolation and purification, i.e. isolation and purification according to the solubility, adsorbency and size.

Conventional methods generally employed in searching biologically active materials are as follows: First, water-soluble or oil-soluble materials are isolated according to their physical or chemical properties. And pharmaceutical or biological activities are assayed on the crude extract obtained using adsorption chromatography, thin layer chromatography, gel filtration chromatography and/or ion exchange chromatography. Then, additional extraction and isolation using said chromatographies is conducted on the fraction of crude extract showing specific activity, and finally the biologically active compounds are isolated and purified.

But in the pharmaceutical or biological assays of unpurified crude extracts, there can be errors due to the additive effect which often shows more excellent activity than that of the single compound.

In addition, said methods of searching biologically active materials have defect in that since the methods use extraction, isolation and purification several times on the general compounds, the method cannot find biologically active materials which exist in small amounts in extract.

DISCLOSURE OF INVENTION

Therefore, among to one aspect of the present invention, there is provided easy and inexpensive method for preparing libraries using compounds from natural products, which is different from the conventional library preparation method which depends largely on organic synthesis.

According to another aspect of the present invention, there is provided a method for quickly discovering useful components by using chemical binding specificity of compounds contained in crude extracts not by random isolation or purification in searching useful new drug component or biological substance from natural products such as herbal drugs.

According to still another aspect of the present invention, there is provided a method constructing numerous libraries that are difficult to obtain by conventional organic synthesis method using various compounds from natural products to overcome the limits in number and structure of said conventional method.

According to further aspect of the present invention, there is provided a method for preparing a focused library from natural products using the compound whose structure and function is known, as an anchor compound.

According to still further aspect of the resent invention, there is provided method for discovering new drugs and functional biological substances easily and quickly by using general and focused libraries firm crude extracts of natural products prepared by said method.

BEST MODE FOR CARRYING OUT THE INVENTION

The object of the present invention is to provide a novel library of compounds from natural products and the method of use thereof, in a completely different way from the conventional methods, by combining the conventional combinational chemical method including the development of new drugs and biological substances, which has depended only on the organic synthesis method and the natural products research method, which has depended only on isolation and purification.

As described above, in searching for biologically active substances from natural products, researchers usually used methods, wherein new biologically active substances are discovered by isolation and purification according to their physical and/or chemical properties and by structural analysis. However, the present invention employs a method of easily isolating compounds from natural products, wherein crude extracts are isolated according to their chemical reactivities using materials which can be used as supports of solid phase synthesis (hereinafter referred to as "solid phase resin"). So, various kinds of compound libraries (same as "general library" in the description and claims) from natural product for use in searching can be manufactured in a short time by sorting compounds having specific functional groups from many compounds of natural products using the solid phase resin, and these libraries can be utilized in the development of new drugs and functional biological substances.

Also, when the structure of a compound which interacts selectively on a specific target is already known, this known compound (hereinafter refereed to as an "anchor compounds") is coupled to the solid phase resin and reacted with crude extracts of natural products to produce a focused library wherein the compound from natural products is attached to the anchor compound. In another way, a focused library from natural products can be manufactured by coupling an anchor compound to the solid phase resin and then reacting with said general library.

The present invention provides a compound library preparation method from natural products using solid phase synthesis comprising the steps of: (a) attaching exit of natural product to the solid phase resin; and (b) washing the compounds and reactants, which are not attached.

The present invention also provides a compound library preparation method comprising the steps of: (a) attaching extra of natural product to the solid phase resin; (b) blocking to exclude a specific functional group from a extract of natural products; and (c) washing the compounds and reactants, which are not attached.

The present invention also provides a library preparation method comprising the steps of: (a) attaching extract of natural product to the solid phase resin; (b) blocking to exclude a specific functional group from a extract of natural products; (c) washing the compounds and reactants, which are not attached an added step of cleaving the bond between the solid phase resin and the compound, after the step of said washing.

The present invention also provides a compound library preparation method comprising an added step of cleaving said compound attached from the solid phase resin, after the step of washing in said methods.

The present invention also provides a library preparation method from natural products using solid phase synthesis, comprising the steps of: (a) attaching a known anchor compound to the solid phase resin; (b) blocking to exclude a specific functional group from the crude extract of natural products; (c) reacting said blocked crude extract with the solid phase resin to which said anchor compound is attached; and (d) washing.

The present invention also provides a library preparation method from natural products comprising an added step of cleaving said anchor compound to which the natural compound is attached from the solid phase resin, after the step of washing.

And, the present invention also provides a library from natural products, prepared by said methods.

And, the present invention also provides a method for searching or optimizing a biologically active substance including an enzyme inhibitor and a receptor ligand by using the said library.

A general library preparation method using crude extracts from natural products is detailed below:

First, extraction from natural product is carried out with water or organic solvent and, if required, blocking is carried out to exclude specific functional groups from the crude extracts. For example, a specific functional group can be blocked using a blocker, which can operate selectively on various functional groups of compounds included in the crude extend such as an alcohol, phenol, carbonyl, carboxyl, and amine groups.

Representative chemical reactions and blocking groups which block the alcohol group in a compound having an alcohol group or in various functional groups of one compound are shown in Table 2, and chemical reactions and blocking groups which block a phenol group from phenols or compounds are shown in Table 3. Chemical reactions and blocking groups which block a carbonyl group which can be reacted by a base and nucleophile are shown in Table 4, and chemical reactions and blocking groups which block a carboxyl group shown in Table 5. Chemical reactions and blocking groups, which block an amine group, which can be reacted by an acid radical, and electrophile are shown in Table 6. Chemical cons and blocking groups shown in the Tables 2 trough Table 6 are illustrative and are not intended to limit the scope of the present invention to these chemical reactions and blocking groups shown in said tables.

Next, said crude extract is attached to the solid phase resin.

Thirdly, washing is carried out to remove the crude extract that is not attached to the solid phase resin and excess reagents and solutes. After washing it for several times with solvent such as methanol and dichloromethane, the resin is dried under reduced pressure or at a room temperature.

Finally the bond between the solid phase resin and the compounds attached thereof is cleave. In this way, a library from natural products having the similar chemical binding property can be generated. Also, if required, a library, which is coupled with the solid phase resin, can be generated and used without said step of cleaving.

In addition, a focused library preparation method using the herbal drugs and compounds of crude extracts is detailed below. The focused library can be obtained by attaching a compound whose structure is known to the solid phase resin, and carrying out said steps of the library preparation method First, the known compound that reacts selectively with a specific target, e.g. an anchor compound, is attached to the solid phase resin and is washed.

Next, the specific functional group of crude extracts is blocked.

Thirdly, the crude extract in which said specific functional group is blocked is reacted with the anchor compound attached to the solid phase resin.

Fourthly the crude extract which is not reacted with the anchor compound, and excess reagents or solutes are removed by washing, and is dried under reduced pressure or at a room temperature.

Finally, the bond between the solid phase resin and the anchor compound attached thereof is cleaved. In this way, the focused library from natural products, which is coupled with the anchor compound that reacts selectively with the specific target, can be generated. Also, if required, the focused library which is coupled with the solid phase resin can be generated and used without said steps of cleaving.

In addition, chemical libraries from neutral products prepared by said method, that is a general library and focused library can be used in searching or optimizing the biologically active substances including enzyme inhibitors and receptor ligands by the conventional combinational chemical method.

The foregoing may be better understood by references to the following examples, which are provided for illustration and are not intended to limit the scope of the present invention.

EXAMPLE 1

In order to obtain a natural compound, which has a carboxyl group that can be combined with amine, from the white bark of an elm tree, 500 g of said bark was ground into powder. Then, this 500 g of powder was maintained in 2l of 80% methanol solution for a day. Then, the extract filtrate was separated from the precipitate using a high-speed centrifugal separator (880 rpm for 20 minutes), and thus obtained supernatant liquid was concentrated and dried in vacuum under educed pressure.

In order to block the amine group in the dried powder extract, 5 g of said dried extract was dissolved in 10 ml of N,N-dimethylformamide. To this was added 1 ml of acetyl anhydride, and the mixture was reacted for three hours. After the reaction, the reaction mixture was diluted with 50 ml of distilled water and extracted with 100 ml of ethyl acetate. The organic layer was washed successively with 100 ml of 10% aqueous solution of hydrochloric acid, 100 ml of said sodium bicarbonate and 100 ml of saturated sodium chloride, and died with sodium sulfate anhydride, and then the solvent was removed under reduced pressure to give 5.1 g of the dried extract mixture (I) from which an amine group had been blocked.

5.1 g of said extract mite (I) was dissolved in 30 ml of acetone. Then, in order to block the alcohol group in the extract mixture (I), 0.5 g of 3 mmol p-toluene sulfonic acid was added, and the mixture was stirred for 2 hours at room temperature. The mixture was diluted with 50 ml of distilled water and extracted with 100 ml of ethyl acetate. The organic layer was washed successively with 100 ml of 10% hydrochloric acid solution, 100 ml of saturated sodium bicarbonate and 100 ml of saturated sodium chloride, then dried with sodium sulfate anhydride, and then the solvent was removed under reduced pressure to give 5.2 g of the solid mixture (II) from which an alcohol and amine groups had been blocked.

To link an acid radical contained in said solid mixture (II) to an amine group in the resin, 5.2 g of solid mixture (II) was dissolved in 1 ml of N-methyl pyrrolidone and 500 mg of the Wang resin (0.4 mmol/g) substituted with cysteine was added 2 mmol of dicyclobexylcarbodiimide and 2 mmol of N-hydroxybenzotriazole were added, and the mixture was reacted for 12 hours at room temperature.

After conforming the absence of amine in the resin through amine color reaction (Kaiser Test; E. Kaiser, et al. Anal. Biochem., 1970, 34, 595), the unreacted solid mixture (II) and dicyclohexyl urea and N-hydroxybenzotriazole were removed from the resin by filtering. The resin was washed tree times with 50 ml of 98% methanol and 50 ml of dichloromethane and was completely dried at room temperature to give 549 mg of the resin.

549 mg of resin thus obtained was placed in 5 ml of triisopropyl acetic acid and 0.01 ml of triisopropyl silane for 30 minutes so that the compound could be isolated from the resin. The reagent was dried under reduced pressure to produce a focused library having a structure containing cysteine group.

EXAMPLE 2

To obtain a library containing an alcohol group from the solid mixture (I) prepared in Example 1(an extract from the white bark of an elm tree), 5 g of the solid mixture (I) was dissolved in 30 ml of dried terahydrofurane, and to this was added 1 g of the Wang resin (0.88 mmole/g), and the mix was sired for 4 hours under the Mitsunobu reaction condition (Porco, J. A.,; Deegan, T.; Devonport et al Molecular Diversity., 1996, 2, 197–206).

After the reaction, the resin was washed with 100 ml of 98% methanol and 100 ml of dichloromethane respectively and completely dried to give 1.02 g of the resin to which was attached a compound containing an alcohol group.

The dried resin was reacted with 95% trifluoro acetic acid for an hour, then the general compound library containing alcohol group was isolated, and the solvent was completely removed under reduced pressure and dried to yield a general library containing an alcohol group.

EXAMPLE 3

500 g of white bark of an elm tree was ground into powder and was maintained in 2l of 80% methanol solution for a day. Then, the extract filtrate was separated from the precipitate using a high-speed centrifugal separator (880 rpm for 20 minutes), and thus obtained supernatant liquid was concentrated and dried in vacuum under pressure.

To obtain a library containing an amine group, 5 g of said dried extract was dissolved in 30 ml of dried dichloromethane, and the mixture was added to the solution with 1 g of 2-chloro trityl resin (0.85 mmol/g), and then 0.5 ml of N,N-diisopropyl amine was added slowly.

It was raced for 2 hours at room temperature, followed by filtering the resin, and was washed several times with 50 ml of dichloromethane.

1.04 g of the dried resin to which an amine group had been attached were treated with the 2% trifluoro acetic acid/ dichloromathane solution to cleave the resin, and so the compound was isolated. The library containing an amine group was dried under reduced pressure to yield a general library containing an amine group.

EXAMPLE 4

500 g of Acanthopanax was ground into powder and was maintained in 2l of methanol solution for a day. Then, the extract filtrate was separated from the precipitate using a high-speed centrifugal separator (880 rpm for 20 minutes), and thus obtained supernatant liquid was concentrated and dried in vacuum under reduced pressure.

To eliminate hydrophilic compounds and very hydrophobic compounds, said Acanthopanax extract is suspended in water and extracted by adding normal hexane 400 ml. The hexane fraction is disposed to eliminate very hydrophobic compounds, and the water fraction is extracted by adding ethyl acetate 600 ml to eliminate hydrophilic compounds in water fraction. An anhydrous magnesium sulfate is added to the said organic fraction and filtered. An extract of 4 g is obtained by drying under reduced pressure.

1 g of said Acanthopanax extract is dissolved in 5 g of methylene chloride and 24 mg of 2-chlorotrityl chloride resin (0.885 mmol/g) is added, and 0.5 mg of triethylamine is added.

It was reacted for 2 hours at room temperature, followed by filtering the resin, and was washed with a sequence of methylene chloride, water, methanol, hexane, and washed by methylene chloride again, and died.

Said dried resin were treed with the 5% trifluoro acetic acid/methylene chloride solution to cleave the resin, and so the compound was isolated. Said solution was extracted by adding water and methylene chloride solution. The library was dried under reduced pressure to yield a general library. An anhydrous magnesium sulfate is added to the said organic fraction and filtered. A compound library of 5.6 mg is obtained by drying under reduced pressure.

FIG. 7 represents the results of HPLC analysis of said chemical library obtained from Acanthopanax. Conditions of HPLC are followed.
Buffer solution A: 0.1% TFA in water
Buffer solution B: 0.1% TFA in Acetonitile
Gradient: 0% B 5 min, 0–100% B 20 min at the flow me of 1 ml/min, monitoring at 214 nm.
Column; Waters reverse-phase C18 column (3.9×150 mm)

Figure 1:
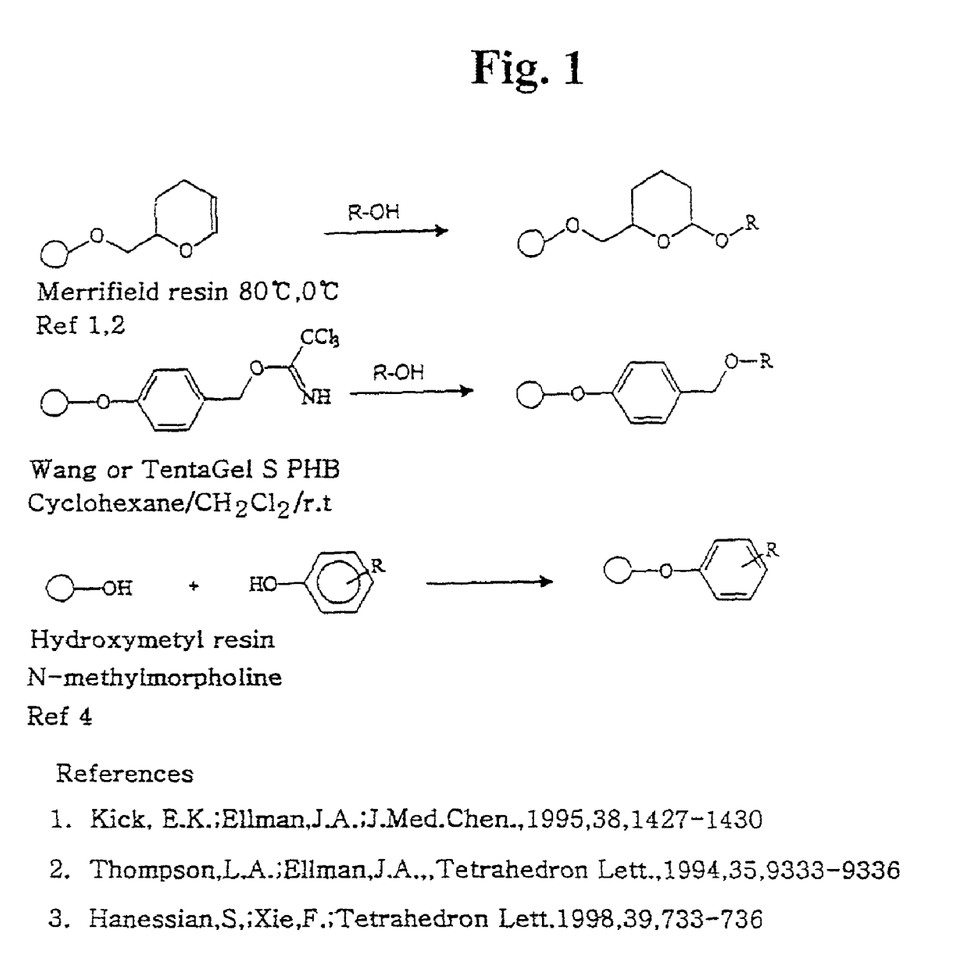
FIG. 1 illustrates examples of chemical reactions of solid phase resin with compounds containing alcohol groups.
Figure 2A:
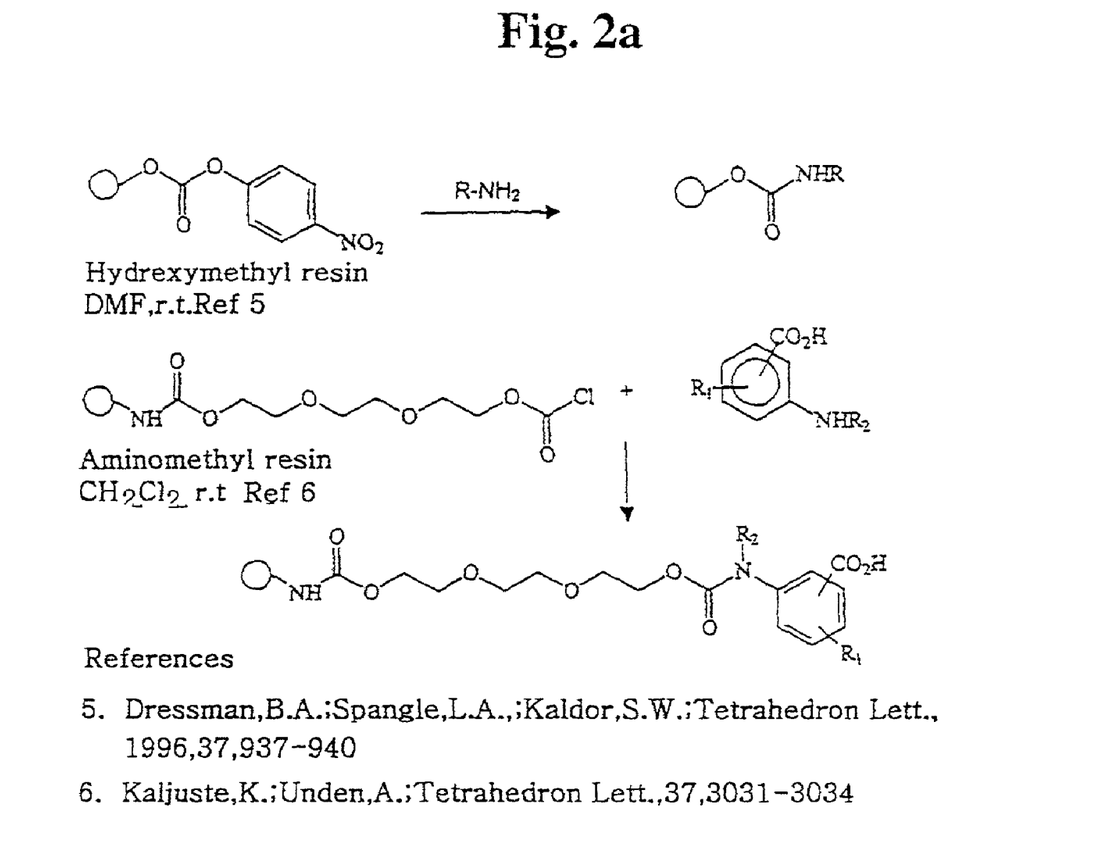
FIGS. 2a and 2b illustrate examples of chemical reactions of solid phase resin with compounds containing amine groups.
Figure 2B:
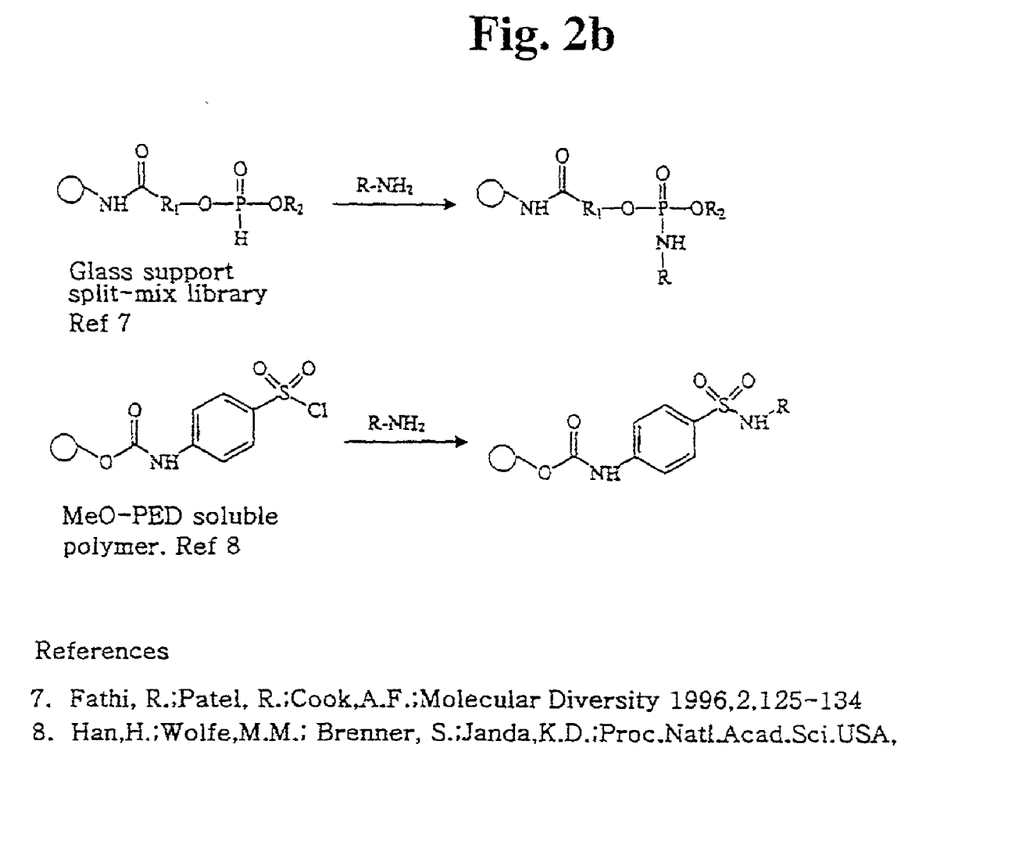
Figure 3:
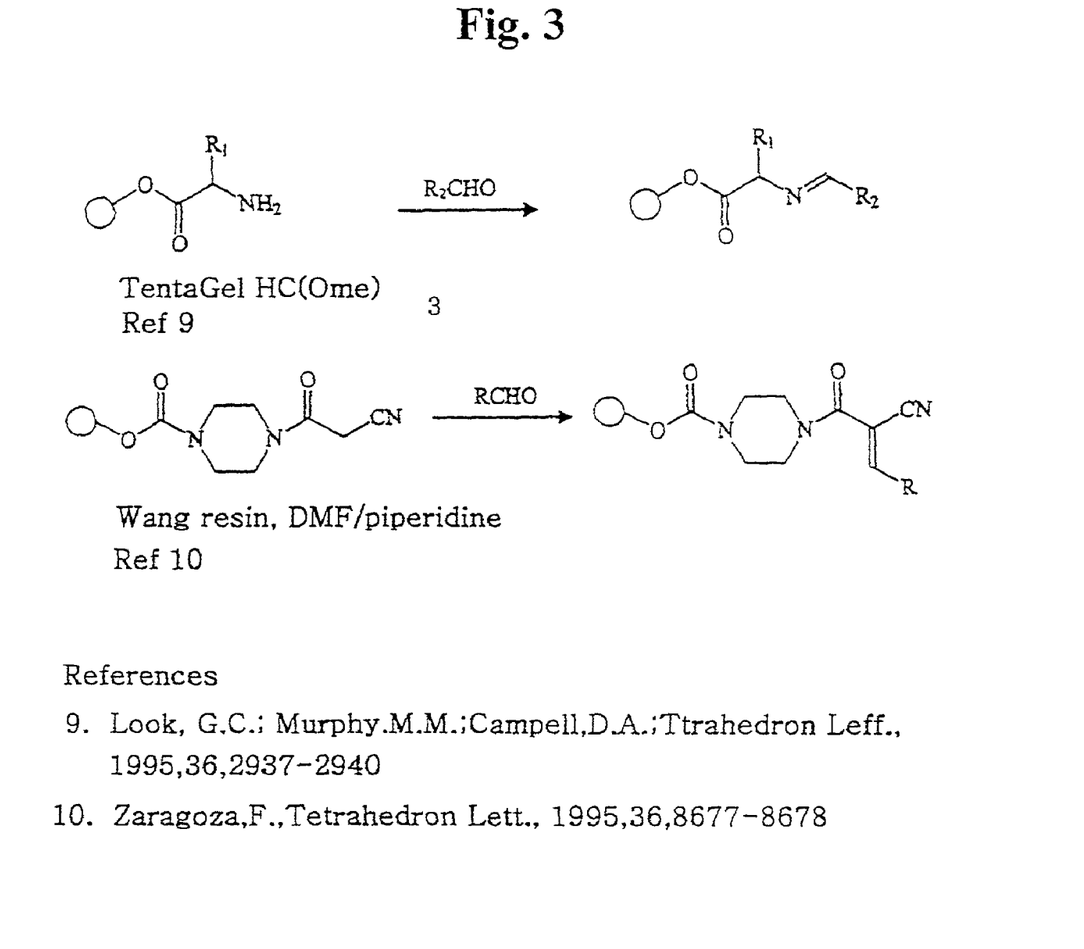
FIG. 3 illustrates examples of immunization reaction of resin containing amine groups with compounds containing aldehyde groups.
Figure 4:
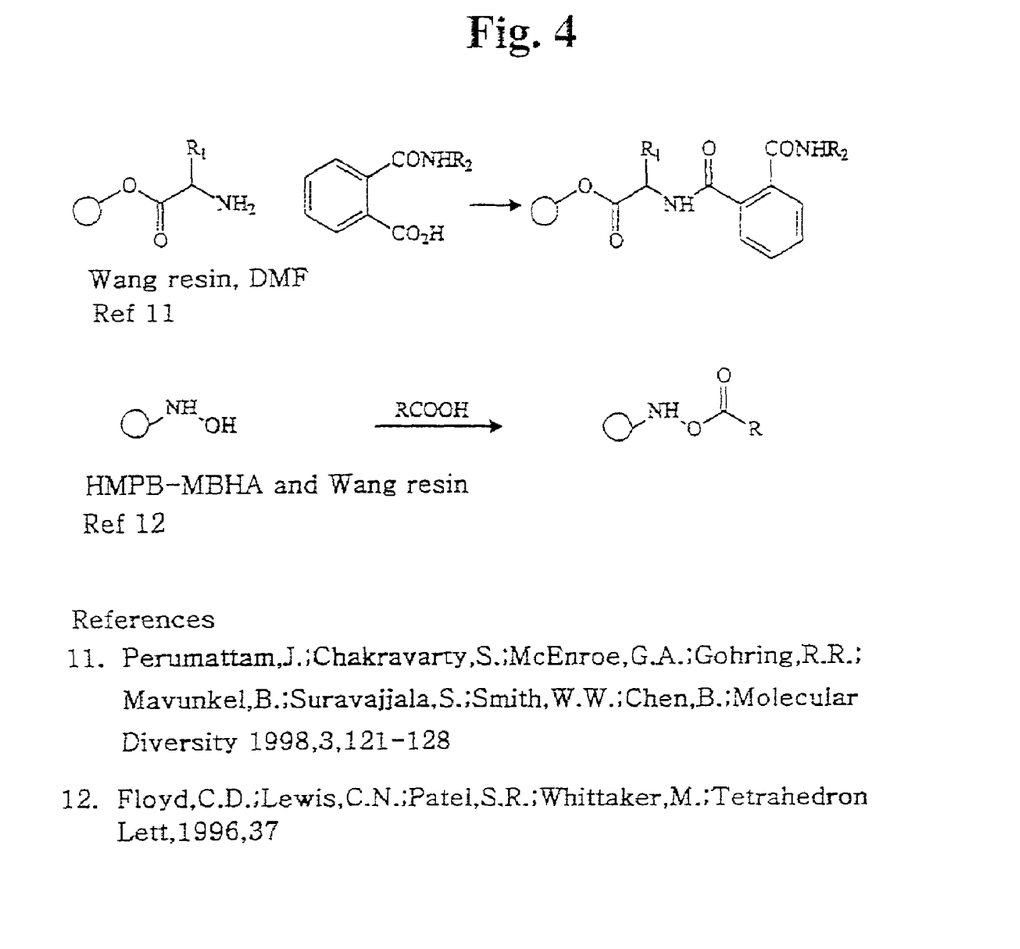
FIG. 4 illustrates examples of a condensation reaction of resin containing amine or alcohol groups with compound containing carboxyl group.
Figure 5:
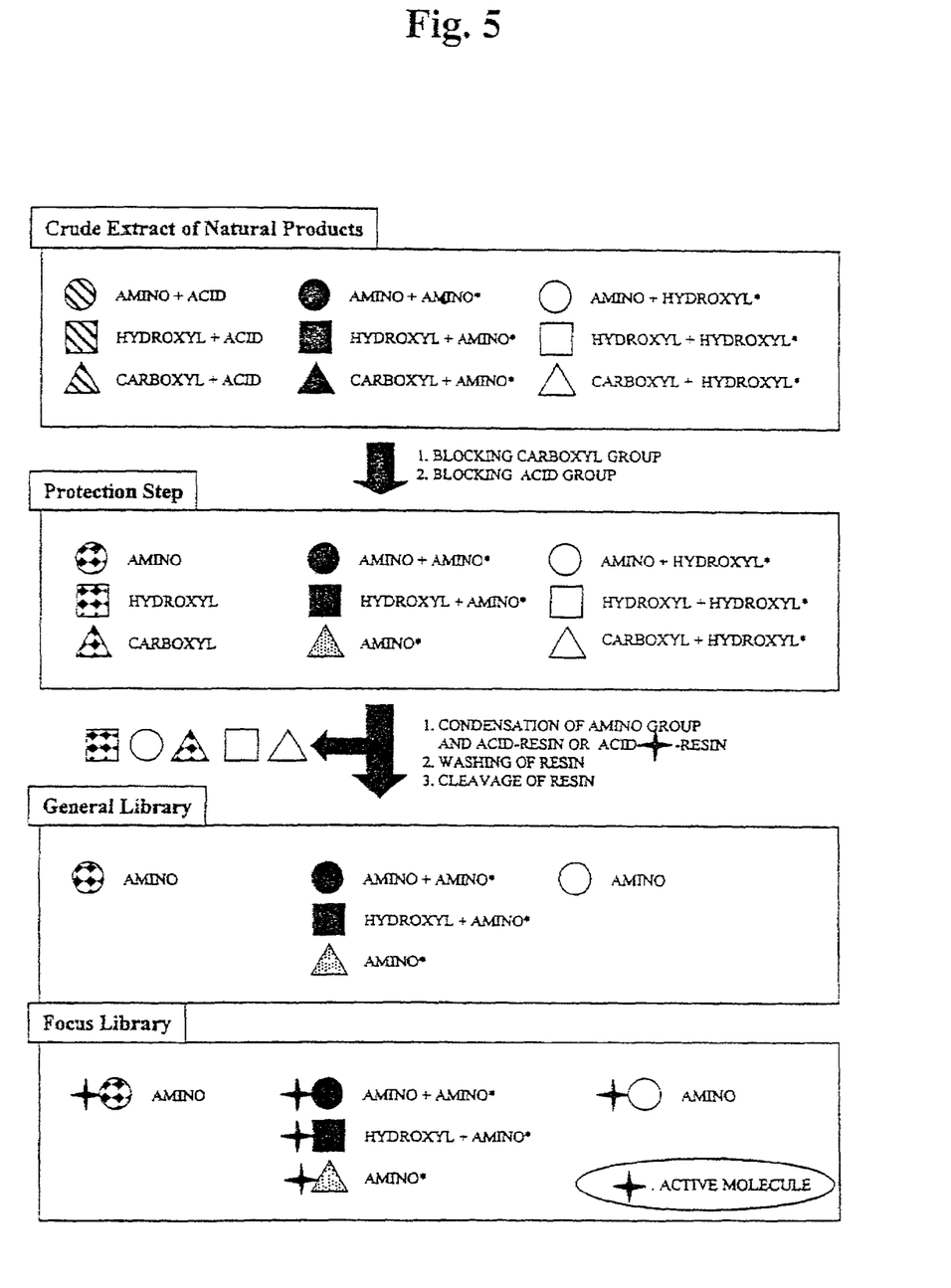
FIG. 5 is a conceptual diagram of the method of the present invention for manufacturing a compound library from natural products.
Figure 6A:
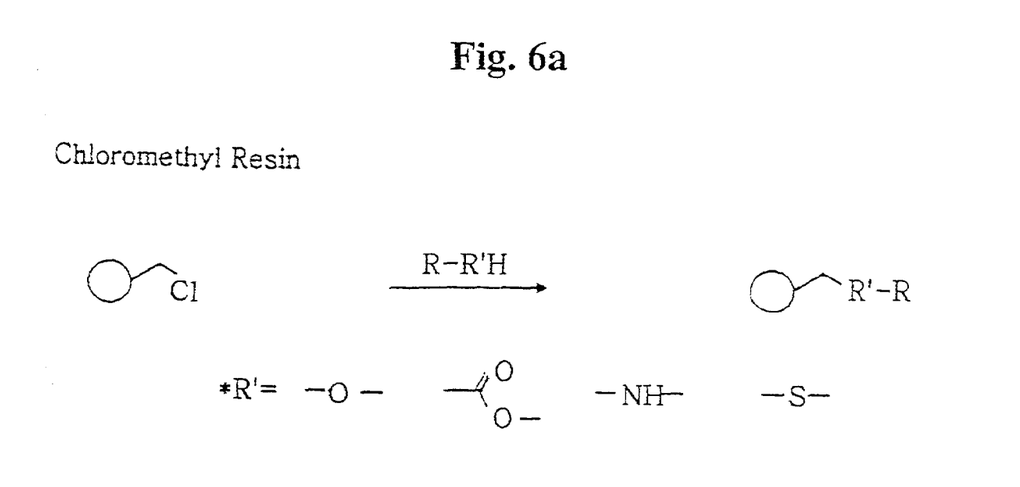
FIG. 6 illustrates examples of a chemical reactions of solid phase resin with compounds containing functional groups which can react with halogen.
Figure 6B:
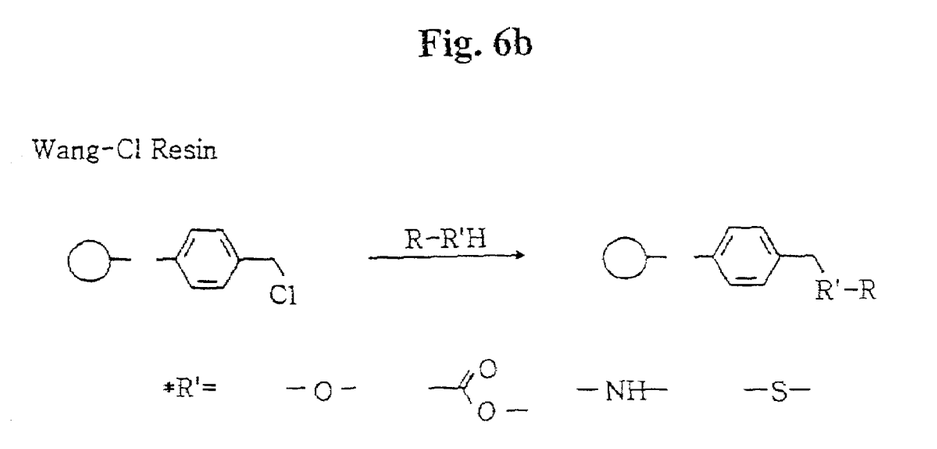
Figure 6C:
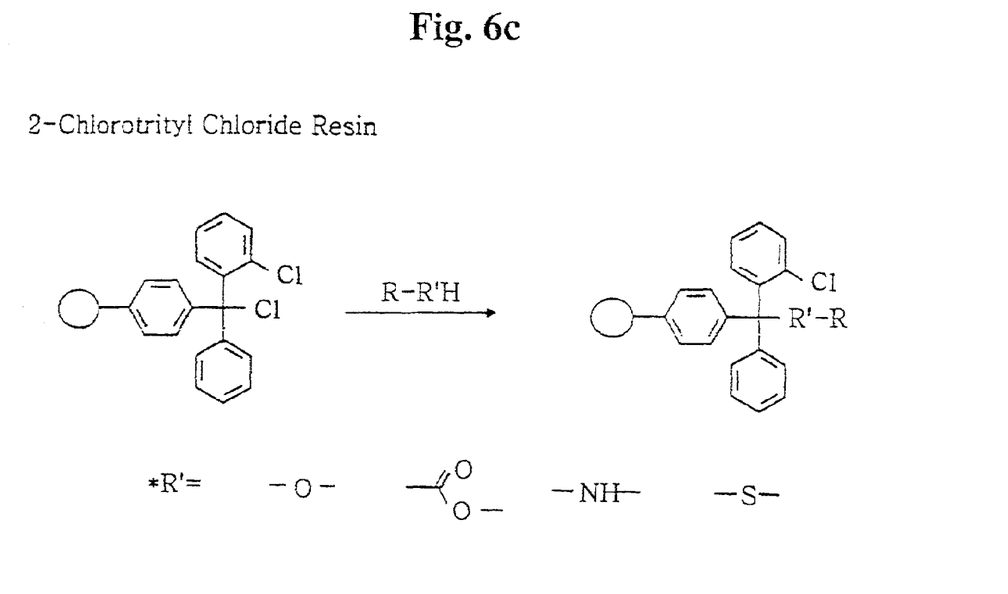
Figure 7A:
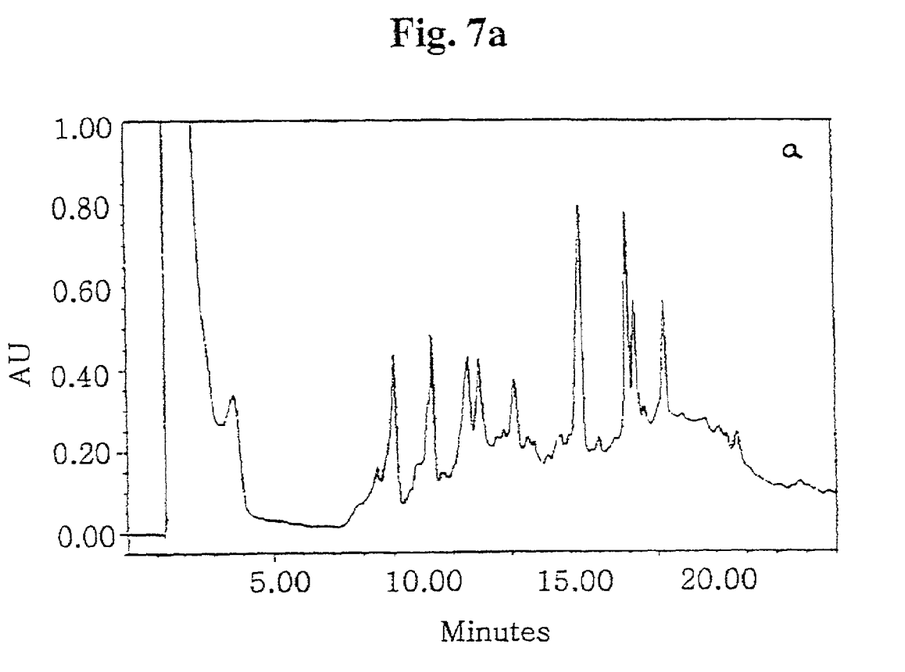
FIG. 7. is HPLC analysis of chemical library obtained from Acanthopanax.
Figure 7B:
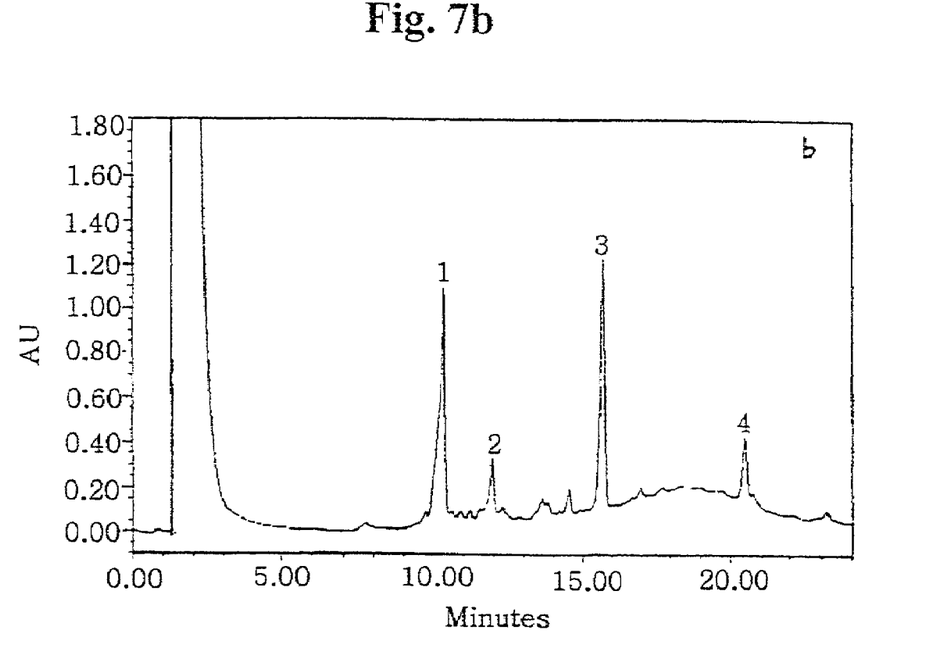

FIG. 7a represents HPLC analysis of an Acanthopanax extract by ethyl acetate, and FIG. 7b represents HPLC analysis of said compound library of Acanthopanax.

In that result, 4 compounds are the major components in said library. FIG. 7b, peak 1,2,3,4). A result of LC-MASS represents the molecular weight of peak 1, 2, 3 and 4 are 532, 441, 495 and 988, respectively.

EXAMPLE 5

To measure the inhibitory effect of the focused library prepared in Example 1 to the Hepatitis C virus protease, each compound in the library were purified by reverse-phase HPLC and dissolved in DMSO in the concentration of 1 mg/ml.

Fluorogenic HCV protease substrate having the amino acid sequence of (Dabcyl) EDVVPCSMSE (Edans) was synthesized and dissolved in the assay buffer (50 mM Tris-HCl(pH 7.6), 10 mM DTT, 30% glycerol, 2% CHAPS) in the concentration of 10 uM.

Recombinant Hepatitis C virus protease was dissolved in the assay buffer in the concentration of 15 nM. 60 ul of enzyme solution was placed on a 96 well plate and 10 ul of library solution was added. After incubation for 10 minute at room temperature 30 ul of fluorogenic substrate was added and fluorescence intensity was measured by fluorometer at the extinction wavelength of 355 nm and the emission wavelength of 485 nm.

The library construction (same as "preparation") method according to the present invention has some advantages in comparison with the conventional library construction methods.

First, when constructing the various libraries by using the conventional methods, it inevitably costs a lot to purchase many compound components since these methods produce various molecules by combining with the compound components of various structures, systematically and repeatedly, according to their structures. And, in the case of using the known compound components, it might already been synthesized by other researchers so that there was a possibility of much waste due to duplicated research.

On the other hand, by using the compounds from natural products, the cost for purchasing the compound components can be reduced since many compounds from one natural product can become compound components, necessary in the library, by covalently attaching them to the specific groups in solid, thereby reducing the cost Representative solid phase resins that can capture the compounds according to their chemical characteristics are classified by their chemical properties in Table 1.

Next, according to the library preparation method of the present invention, a lot of libraries, wherein classified specific group such as amine, imine, carbonyl, aldehyde, olefin, and alcohol groups by which organic compounds can participate in the reaction trough chemical selective reactions are classified, can be economically constructed from one natural product.

Thirdly, while in using the commercially available compound components in the conventional method, it was not so easy to construct a library other than the library already manufactured by many combinatorial chemists, and the library using the method of the present invention can involve compounds which are difficult to synthesize artificially under current technology.

TABLE NO. 1

| | |
|---|---|
| Base scavenger resin |  |
| Acid or electrophilic scavenger resin |  |
| |  |

TABLE NO. 1-continued

Nucleophilic scavenger resin

TABLE NO. 2

| Types of blocking | Product forms | Reaction conditions | Ref |
|---|---|---|---|
| Methyl Ether | ROMe | $CH_2N_2$, silicagel, $Et_2O$ | 1 |
|  |  | MeI, $Ag_2O$, | 2 |
| Substituted Methyl Ethers | MOM | $CH_3OCH_2Cl$, NaH, THF | 3 |
| Substituted Ethyl Ethers | EEOR | Ethyl vinyl ether, TsOH, 25°, 1 h | 4 |
|  | t-BuOR | Isobutylene, $BF_2Et_2O$, $H_3PO_2$ | 5 |
|  | p-$ClC_6H_4$OR | MsCl, Pyr, p-$ClC_6H_4$ONa | 6 |
|  | BnOR | BnI, NaH, rt | 7 |
| Substituted Benzyl Ether | MPMOR | NaH, p-$MeOC_6H_4CH_2Br$, DMF | 8 |
| Silyl Ethers | $ROSi(CH_3)_3$ | $Me_3SiCl$, $Et_3N$, THF | 9 |

Ref
1. T. Nakata, S. Nagao, N. Mori, and T. Oishi, Tetrahedron Lett., 1985, 26, 6461
2. A. E. Greene, C. L. Drian, and P>Crabbe, J. Am. Chem. Soc., 1980, 102, 7583
3. A. F. Kluge, K. G. Untch, and J. H. Fried, J. Am. Chem. Soc., 1972, 94, 7827
4. A. L. Meyers, D. L. Comins, D. M. Roland, R. Henning, and K. Shimizu, J. Am. Chem. Soc., 1979, 101, 7104
5. H. C. Beyeman and G. L. Heiszwolf, J. Chem. Soc., 1963, 755
6. J. A. Marshall and J. J. Partridge, J. Am. Chem. Soc., 1968, 90, 1090
7. E. E. Van Tamelen, S. R. Zawacky, R. K. Russell, and J. G. Carlson, J. Am. Chem. Soc., 1983, 105, 142
8. H. Takaku and K. Kamaike, Chem. Lett., 1982, 189
9. E. J. Corey and B. B. Snider, J. Am. Chem. Soc., 1972, 94, 2549

TABLE NO. 3

| Types of blocking | Product forms | Reaction conditions | Ref |
|---|---|---|---|
| Ether | $ArOCH_3$ | MeI, $K_2CO_3$, acetone | 1 |
| Silyl Ethers | $ArOSi(CH_3)_3$ | $Me_3SiCl$, Pyr, 30–35° | 2 |
| Esters | $ArOCOCH_3$ | 1-Acetyl-v-triazolo[4,5-b]pyridine, THF, 1N NaOH | 3 |
| Carbonates | $ArOCO_2CH_2C_6H_5$ | $PhCH_2OCOCl$, Pyr, $CH_2Cl_2$, THF | 4 |
| Sulfonates | $ArSO_2C_5H_4$-p-$CH_3$ | TsCl, $K_2CO_3$, acetone, reflux | 5 |

Ref
1. G. N. Vyas and N. M. Shah, Org. synth., 1963, Vol IV, 836
2. S. A. Barker and R. L. Settine, Org. Prep. Proced. Int., 1979, 11, 87
3. M. P. Paradisi, G. K. Makinson, M. O. Naumann, and J. Cunningham, J. Chem. soc., 1964, 2137
4. M. Kuhn and A. Van Wartburg, Helv. Chim. Acta. 1969, 52, 948
5. M. L. Wolfrom, E. W. Koos, and H. B. Bhat, J. Org. Chem., 1967, 32, 1058

TABLE NO. 4

| Types of blocking | Product forms | Reaction conditions | Ref |
|---|---|---|---|
| Acetals and | $R_2C(OCH_3)_2$ | $CH(OMe)_3$, $MeNO_2$, $CF_3CO_2H$ | 1 |
| Cycle Acetals |  | $HO(CH_2)_3OH$, TsOH, benzene | 2 |
| Dithio Acetals and Ketals | $R_2C(SCOCH_3)_2$ | $CH_3COSH$, 6N $H_2SO_2$, 25° | 3 |
| Monothio Acetals and Ketals | $R_2C(SR')OSiMe_3$ | $Me_3SiCl$, R'SH, Pyr, 25° | 4 |

Ref
1. A. Thurkauf, A. E. Jacobson, and K. C. Rice, Synthesis, 1988, 223
2. H. Okawara, H. Nakai, and M. Ohno, Tetrahedron Lett., 1982, 23, 1087
3. T. Kametani, Y. Kigawa, K. Takahashi, H. Nemoto, and K. Fukumoto, Chem. Pharm Bull., 1978, 26, 1918
4. T. H. Chan and B. S. Ong., Tetrahedran Lett., 1976, 319

TABLE NO. 5

| Types of blocking | Product forms | Reaction conditions | Ref |
|---|---|---|---|
| Methyl Esters | $RCO_2CH_3$ | $Me_3SiCHN_2$, MeOH, benzene | 1 |
| t-Butyl Esters | $RCO_2C(CH_3)_3$ | (t-BuO)$_2$CHNMe$_2$, toluene, 80° | 2 |
| Benzyl Eters | $RCO_2CH_2C_6H_4$ | BnOCOCl, $Et_3N$, DMAP, $CH_2Cl_2$ | 3 |
| Silyl Esters | $RCO_2Si(CH_3)_3$ | $Me_3SiCl$, Pyr, $CH_2Cl_2$, 30° | 4 |
|  | $RCO_2Si(CH_3)_2C(CH_3)_3$ | Morpholine, TBDMSCl, THF | 5 |

Ref
1. T. Hiral, T. Aida, and S. Inoue, J. Am. Chem. Soc., 1989, 111, 3062
2. U. Widmer, Synthesis, 1983, 135
3. S. Kim, Y. C. Kim and J. I. Lee, Tetrahedron Lett., 1983, 24, 3365
4. B. Fechti, H. Peter, H. Bickel and E. Vischer, Helv. Chim. Acta, 1968, 51, 1108
5. I. W. Perich and R. B. Johns, Synthesis, 1989, 701

TABLE NO. 6

| Types of blocking | Product forms | Reaction conditions | Ref |
|---|---|---|---|
| Carbamates | Fmoc-$NR_2$ | Fmoc-OSu, $H_2O$, $CH_3CN$ | 1 |
|  | $(CH_3)_3COC(O)NR_2$ | $(Boc)_2O$, NaOH, $H_2O$ | 2 |
| Urea Type | $R_2NCONHSO_2C_6H_4$-p-$CH_3$ | p-Tosyl isocyanate | 3 |
| N-Formyl | $R_2NCHO$ | $HCO_2Et$, heat | 4 |

TABLE NO. 6-continued

| Types of blocking | Product forms | Reaction conditions | Ref |
|---|---|---|---|
| N-Aceyl | R$_2$NAc | Ac$_2$O, 18-crown-6, Et$_3$N | 5 |
| N-Benzyl | C$_6$H$_5$CH$_2$—NR$_2$ | BnCl, KH, THF | 6 |

Ref
1. A. Paquet, Can. J. Chem., 1982, 60, 976
2. D. S. Tarbell, Y. Yamamoto and B. M. Pope, Proc. Natl. Acad. Sci USA, 1972, 69, 730
3. B. Weinstein, T, N. S. Ho, R. T. Fukura and E. C. Angell, Synth. Commun., 1976, 6, 17
4. H. schmidhammer and A. Brossi, Can. J. Chem., 1982, 60, 3055
5. A. G. M. Barrett and J. C. A. Lana, J. Chem. Soc., Chem. Commun., 1978, 471
6. Y. Xia and A. P. Kozikowski., J. Am. Chem. Soc., 1989, 111, 4116

What is claimed is:

1. A method for preparing a compound library from natural products, comprising the steps of:
    (a) covalently binding an extract of a natural product to solid phase resin; and
    (b) eluting substances from said extract of a natural product, which are not covalently bound to said solid phase resin and
    (c) cleaving the bond between the solid phase resin and substances covalently bound to said solid phase resin.

2. The library preparation method of claim 1, comprising an added step of blocking to exclude a specific functional group from said extract of a natural product from covalently binding to said solid phase resin, before the step of said covalently binding.

3. A library preparation method from natural products, comprising the steps of:
    (a) covalently binding an anchor compound to a soldi phase resin;
    (b) covalently binding a crude extract of a natural product to said anchor compound which are covalently bound to said solid phase resin;
    (c) eluting substances from said extract of a natural product, which are not covalently bound to said anchor compound; and
    (d) cleaving the bond between the solid phase resin and the anch0or copound covalently bound to said solid phase resin.

4. A library preparation method from natural products, comprising the steps of:
    (a) covalently binding an anchor compound to a solid phase resin;
    (b) covalently binding a crude extract of a natural product to said anchor compound which are covalently bound to said solid phase resin after blocking to exclude a specific functional group from said extract of a natural product from covalently binding to said anchor compound;
    (c) eluting substances from said extract of a natural product, which are not covalently bound to said anchor compound; and
    (d) cleaving the bond between the solid phase resin and the anchor compound covalently bound to said solid phase resin.

* * * * *